US 6,623,452 B2

(54) DRUG DELIVERY CATHETER HAVING A HIGHLY COMPLIANT BALLOON WITH INFUSION HOLES

(75) Inventors: Thomas Yung-Hui Chien, San Jose, CA (US); Henry Nita, Redwood Shores, CA (US); Alain Cornil, Mountain View, CA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/741,278

(22) Filed: Dec. 19, 2000

(65) Prior Publication Data

US 2002/0077594 A1 Jun. 20, 2002

(51) Int. Cl.[7] ............................................. A61M 37/00
(52) U.S. Cl. .......................... 604/103.01; 604/101.01; 604/103.11
(58) Field of Search .................... 604/103.01, 103.1, 604/96.01, 99.01, 99.02, 99.03, 101.01, 101.05, 102.01, 103.11, 164.13, 167.06, 102.03

(56) References Cited

U.S. PATENT DOCUMENTS

| | | | |
|---|---|---|---|
| 4,994,033 A | 2/1991 | Shockey et al. ............. 604/101 |
| 5,049,132 A | 9/1991 | Shaffer et al. ............... 604/101 |
| 5,087,244 A | 2/1992 | Wolinsky et al. ............. 604/53 |
| 5,213,576 A | 5/1993 | Abiuso et al. ................ 604/96 |
| 5,232,444 A | 8/1993 | Just et al. .................... 604/96 |
| 5,527,292 A | 6/1996 | Adams et al. ............... 604/171 |
| 5,538,504 A | 7/1996 | Linden et al. ................. 604/53 |
| 5,554,119 A | 9/1996 | Harrison et al. .............. 604/96 |
| 5,558,642 A | 9/1996 | Schweich, Jr. et al. ....... 604/96 |
| 5,611,775 A * | 3/1997 | Machold et al. ............ 604/509 |
| 5,833,658 A | 11/1998 | Levy et al. |
| 5,843,033 A | 12/1998 | Ropiak ........................ 604/96 |
| 5,843,051 A | 12/1998 | Adams et al. ............... 604/280 |
| 5,866,561 A | 2/1999 | Ungs ........................... 514/182 |
| 5,951,458 A | 9/1999 | Hastings et al. ............... 600/3 |
| 6,050,973 A * | 4/2000 | Duffy ....................... 604/99.02 |
| 6,059,809 A | 5/2000 | Amor et al. |
| 6,120,523 A | 9/2000 | Crocker et al. |
| 6,149,641 A | 11/2000 | Ungs et al. ................. 604/501 |
| 6,231,543 B1 * | 5/2001 | Hedge et al. ............. 604/96.01 |
| 6,280,411 B1 * | 8/2001 | Lennox ................. 604/103.01 |

FOREIGN PATENT DOCUMENTS

EP          0 835 673 A3      9/1997

OTHER PUBLICATIONS

U.S. patent application Ser. No. 09/311,446, Patterson et al., filed May 14, 1999.

* cited by examiner

Primary Examiner—Brian L. Casler
Assistant Examiner—Mark K. Han
(74) Attorney, Agent, or Firm—Crompton, Seager & Tufte, LLC

(57) ABSTRACT

An intravascular drug delivery balloon catheter incorporating a highly compliant balloon having a plurality of infusion holes. The highly compliant balloon elastically expands at a low inflation pressure (e.g., less than 1.0 ATM), and preferably has a compliance of 2.0 mm/ATM or more at pressures less than 2.0 ATM. A pressure relief valve may be incorporated into the catheter to avoid over pressurization. The infusion holes may be open when the balloon is deflated and may enlarge when the balloon is inflated. The balloon may define a single lobe or two inflatable lobes with the infusion holes disposed therebetween.

17 Claims, 2 Drawing Sheets

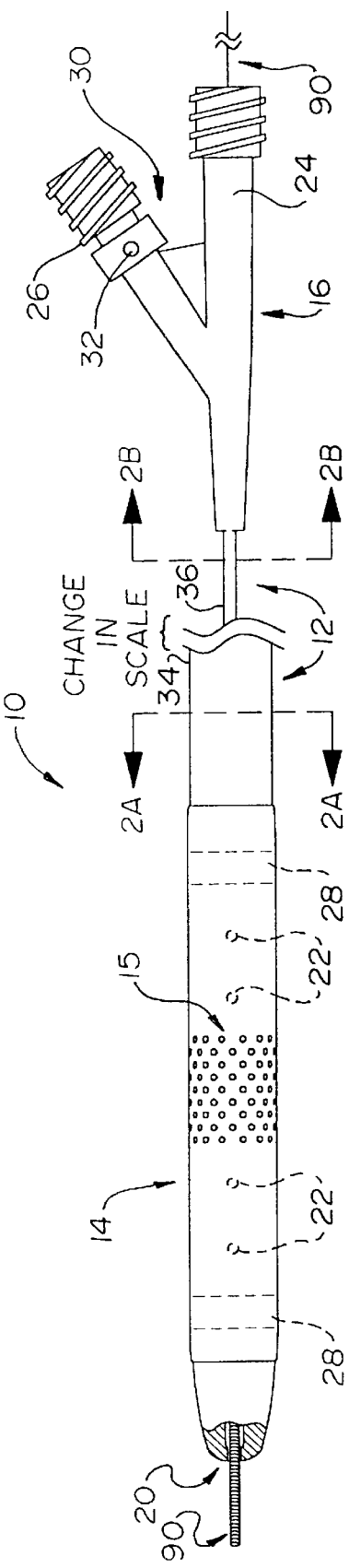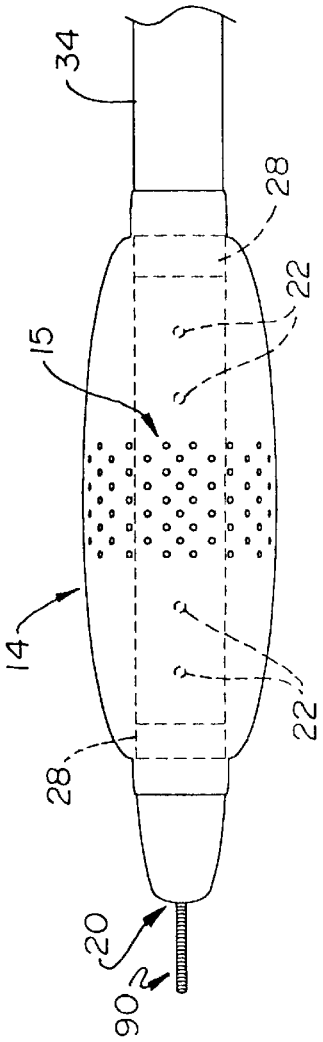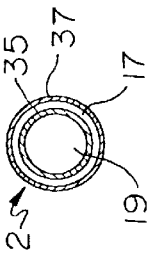

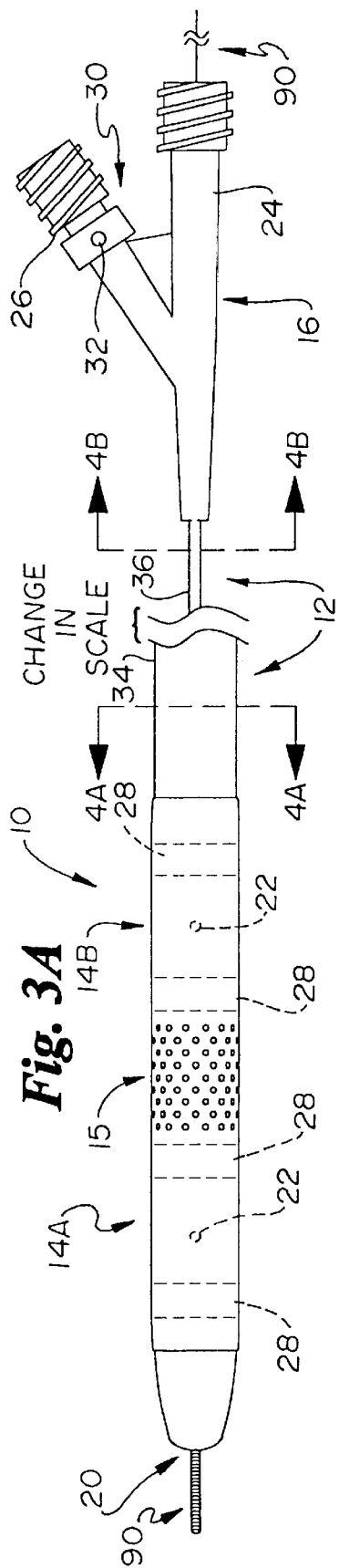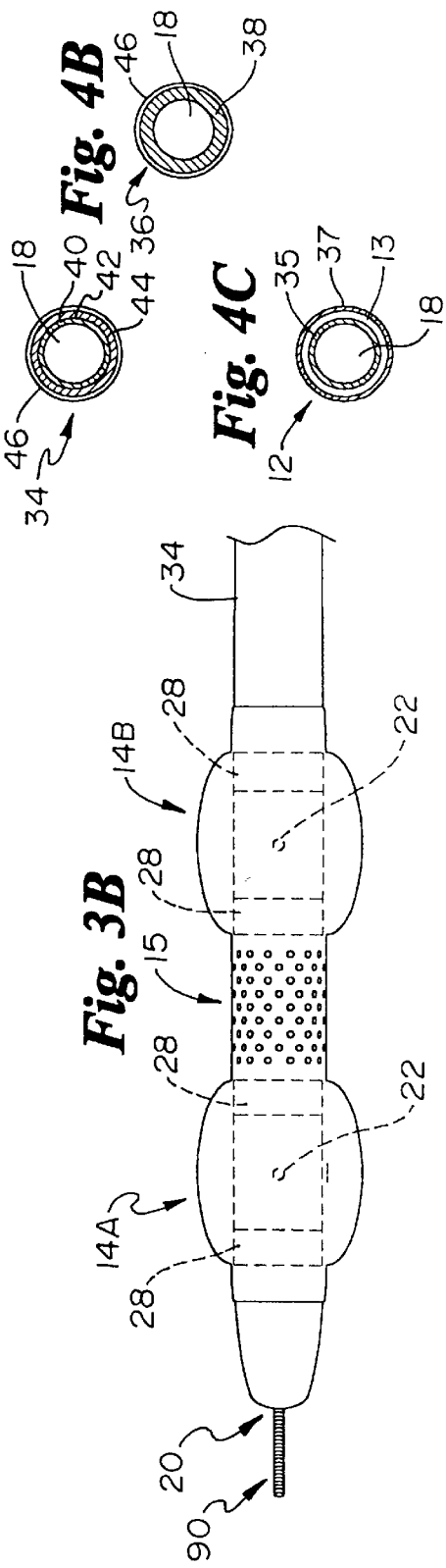

DRUG DELIVERY CATHETER HAVING A HIGHLY COMPLIANT BALLOON WITH INFUSION HOLES

RELATED APPLICATIONS

The present application is related to U.S. patent application Ser. No. 09/311,446, filed May 14, 1999, entitled SINGLE LUMEN BALLOON-TIPPED MICRO CATHETER WITH REINFORCED SHAFT.

FIELD OF THE INVENTION

The present invention generally relates to intravascular drug delivery catheters. More specifically, the present invention relates to intravascular drug delivery catheters having a balloon with infusion holes for the delivery of a fluid drug therethrough.

BACKGROUND OF THE INVENTION

A wide variety of intravascular drug delivery balloon catheters have been proposed for the treatment of vascular disease. An example of an intravascular balloon drug delivery catheter is disclosed in the U.S. Pat. No. 5,087,244 to Wolinsky et al. Wolinsky et al. disclose an over-the-wire type balloon catheter including a thin-walled flexible balloon having a plurality of minute holes through which medication may flow at a relatively low flow rate. Wolinsky et al. state that the balloon may be formed from various polymeric materials and preferably has a thin, flexible, inelastic wall.

In the treatment of certain types of vascular disease, particularly those involving soft occlusive material, vasospasms, and aneurysms, the provision of a drug delivery balloon having an inelastic wall is undesirable. For example, in the treatment of ischemic stroke caused by the formation of a blood clot, the use of an inelastic balloon is not optimal because the balloon does not conform to the soft clot material and may cause accidental dislodgment thereof before medication is delivered. Accordingly, there is an unmet need for an improved drug delivery balloon catheter for the treatment of soft blood clots, vasospasms, aneurysms, and other vascular diseases involving soft tissues.

SUMMARY OF THE INVENTION

To address this unmet need, the present invention provides an intravascular drug delivery balloon catheter and method of use, wherein the catheter incorporates a highly compliant balloon having a plurality of infusion holes. The highly compliant balloon elastically expands at a low inflation pressure (e.g., less than 1.0 ATM), and preferably has a compliance of 2.0 mm/ATM or more at pressures less than 2.0 ATM. A pressure relief valve that vents at pressures above a threshold pressure (e.g., 1.5 ATM) may be incorporated into the catheter to avoid over pressurization of the balloon that may otherwise cause over expansion of the balloon and/or over infusion of the drug. In one embodiment, the infusion holes are open when the balloon is deflated and enlarge when the balloon is inflated. In another embodiment, the balloon defines two inflatable lobes and the infusion holes are disposed between the lobes. The catheter may also include a guidewire seal to accommodate a single lumen design.

BRIEF DESCRIPTION OF THE DRAWINGS

FIG. 1A illustrates a partially sectioned side view of a drug delivery balloon catheter in accordance with an embodiment of the present invention, showing the balloon in the deflated state;

FIG. 1B illustrates a side view of the distal portion of the drug delivery balloon catheter illustrated in FIG. 1, showing the balloon in the inflated state;

FIG. 2A is a cross sectional view taken along line 2A—2A in FIG. 1A;

FIG. 2B is a cross sectional view taken along line 2B—2B in FIG. 1A;

FIG. 2C is an alternative cross sectional view taken along line 2A—2A and line 2B—2B in FIG. 1A;

FIG. 3A illustrates a side view of a drug delivery balloon catheter in accordance with an alternative embodiment of the present invention, showing the balloon in the deflated state;

FIG. 3B illustrates a side view of the distal portion of the drug delivery balloon catheter illustrated in FIG. 3A, showing the balloon in the inflated state;

FIG. 4A is a cross sectional view taken along line 4A—4A in FIG. 3A;

FIG. 4B is a cross sectional view taken along line 4B—4B in FIG. 3A; and

FIG. 4C is an alternative cross sectional view taken along line 4A—4A and line 4B—4B in FIG. 3A.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Refer now to FIGS. 1A, 1B, 2A, 2B, and 2C which illustrate various views of a drug delivery balloon catheter 10 in accordance with an embodiment of the present invention. FIG. 1A illustrates the balloon catheter 10 in the deflated state, and FIG. 1B illustrates the balloon catheter 10 in the inflated state. The drug delivery balloon catheter 10 includes an elongate shaft 12 having a proximal end and a distal end. A manifold 16 is connected to the proximal end of the elongate shaft 12, and a highly compliant balloon 14 is connected to the distal end of the elongate shaft 12. The highly compliant balloon 14 includes a plurality of infusion holes 15 which facilitate the delivery of drugs and other fluids to a specific site in a patient's vascular system.

The proximal and distal ends of the highly compliant balloon 14 are connected to the distal end of elongate shaft 12. In the embodiment illustrated in FIGS. 1A and 1B, the balloon 14 defines a single lobe upon inflation as best seen in FIG. 1B. Alternatively, in the embodiment illustrated in FIGS. 3A and 3B, the mid portion of the balloon 14 is connected to the elongate shaft 12 such that the balloon 14 defines a plurality of lobes 14A/14B upon inflation as best seen in FIG. 3B.

The balloon 14 preferably comprises a highly compliant material that elastically expands upon pressurization. Because the balloon 14 elastically expands from the deflated state to the inflated state, the balloon 14 has an extremely low profile in the deflated state and does not require balloon folding as with other non-compliant or semi-compliant balloon materials. Preferably, the balloon 14 is formed of an extruded thermoplastic polyisoprene rubber such as a 40A durometer hydrogenated polyisoprene rubber which is commercially available under the trade name Chronoperene from CT Biomaterials.

Hydrogenated polyisoprene provides a balloon 14 having superior performance and manufacturing attributes. In particular, hydrogenated polyisoprene may be processed with standard polyolefin processing equipment to obtain balloon tubing having a wall thickness of approximately 0.001 inches to 0.010 inches and a corresponding inside diameter of approximately 0.016 inches to 0.028 inches. Such tubing has been demonstrated to produce balloons having a nominal outside diameter when inflated of approximately 3.0 mm to 5.5 mm.

The highly compliant balloon 14 preferably elastically expands at pressures less than 1.0 ATM. The highly compliant balloon 14 may have a pressure compliance of 2.0 mm/ATM or more at pressures less than 2.0 ATM. If the infusion holes 15 are occluded, the highly compliant balloon 14 may have a volumetric compliance of approximately 0.3 mm per 0.01 ml to 0.5 mm per 0.01 ml at pressures less than 2.0 ATM, for balloons having a nominal diameter of approximately 3.5 mm and a length of approximately 10 mm to 15 mm.

As mentioned previously, the highly compliant balloon 14 includes a plurality of infusion holes 15. The infusion holes 15 may be drilled utilizing a laser drilling technique or other technique known in the relevant art. The infusion holes 15 may be disposed on the inflatable lobe portion of the balloon 14 as illustrated in FIGS. 1A and 1B, or disposed between inflatable lobes 14A/14B as illustrated in FIG. 3A and 3B. In either case, the infusion holes 15 are preferably open when the balloon 14 is deflated. If the infusion holes 15 are positioned on the inflatable lobe portion of the balloon 14, the size of the infusion holes 15 increases as the balloon 14 is inflated.

The size and number of the infusion holes 15 may be selected to allow the balloon 14 to inflate up to a prescribed diameter and to obtain the desired drug infusion rate. The size of the infusion holes 15 may vary along the length of the balloon 14 to correct for pressure drops or to provide an infusion rate gradient along the length of the balloon 14. The infusion holes 15 may extend at an orthogonal angle through the wall of the balloon 14, or at a non-orthogonal to project the drug more distally or more proximally as desired.

The drug delivery balloon catheter 10 is adapted for use in combination with a guide wire 90. The drug delivery balloon catheter 10 may comprise a fixed-wire type balloon catheter or an over-the-wire type balloon catheter as shown. In addition, over-the-wire type embodiments of the drug delivery balloon catheter 10 may incorporate a single lumen design as shown in FIGS. 2A and 2B, or a multi-lumen design as seen in FIG. 2C (e.g., side-by-side dual lumen, coaxial lumens, etc.).

In the single lumen design shown in FIGS. 2A and 2B, the elongate shaft 12 includes a common guide wire/inflation lumen 18 extending therethrough. The common lumen 18 accommodates the guide wire 90 and facilitates inflation/deflation of the balloon 14. A guide wire seal 20 is provided at the distal end of the elongate shaft 12 to provide a fluid seal about the guide wire 90. With this arrangement, inflation fluid passes from the inflation syringe (not shown), through the common lumen 18 around the guide wire 90 disposed therein, through the inflation ports 22, and into the interior of the balloon 14 to facilitate inflation and deflation thereof. Because the infusion ports 15 are in fluid communication with the interior of the balloon 14, the common lumen 18 is used for delivering infusion fluid as well.

The guide wire seal 20 may comprise a gap-type seal or an interference-type seal. A gap-type seal provides a gap around the guide wire 90 that is sufficiently small to inhibit the loss of inflation fluid therethrough, but is sufficiently large to allow free longitudinal and rotational movement of the guide wire 90 therein. An interference-type seal does not provide a gap, but rather provides a contact surface with the guide wire 90 that inhibits loss of inflation fluid therethrough, but has sufficiently low frictional characteristics to allow free longitudinal and rotational movement of the guide wire 90 therein. In either case, the guide wire seal 20 permits the use of a single lumen 18 design which provides a substantially lower profile and substantially improved performance as compared to multi-lumen designs.

In the multi-lumen design shown in FIG. 2C, the elongate shaft 12 includes separate guide wire 19 and inflation 17 lumens extending therethrough. The shaft 12 may be a co-axial design and include an inner member 35 to define the guide wire lumen 19, with the inner member 35 disposed in an outer member 37 to define the annular inflation lumen 17 therebetween. The guide wire lumen 19 accommodates the guide wire 90, and the inflation lumen facilitates inflation/deflation of the balloon 14. In this embodiment, a guide wire seal 20 is not needed since the guide wire lumen 19 is fluidly isolated from the inflation lumen 17. As with the single lumen design, because the infusion ports 15 are in fluid communication with the interior of the balloon 14, the inflation lumen 17 is used for delivering infusion fluid as well.

Similar variants are possible with the embodiment illustrated in FIGS. 3A and 3B. In this embodiment, the catheter 10 may be a single lumen design as shown in FIGS. 4A and 4B, or a multi-lumen design as shown in FIG. 4C.

In the single lumen design shown in FIGS. 4A and 4B, the elongate shaft 12 includes a common guide wire/inflation lumen 18 extending therethrough. The common lumen 18 accommodates the guide wire 90 and facilitates inflation/deflation of the balloon lobes 14A/14B. A guide wire seal (not shown) is provided at the distal end of the elongate shaft 12 to provide a fluid seal about the guide wire 90. With this arrangement, inflation fluid passes from the inflation syringe (not shown), through the common lumen 18 around the guide wire 90 disposed therein, through the inflation ports 22, and into the interior of the balloon lobes 14A/14B to facilitate inflation and deflation thereof. Because the infusion ports 15 are in fluid communication with the common lumen 18, the common lumen 18 is used for delivering infusion fluid as well.

In the multi-lumen design shown in FIG. 4C, the elongate shaft 12 includes a common guide wire/inflation lumen 18, and a separate infusion lumen 13 extending therethrough. The common lumen 18 accommodates the guide wire 90 and facilitates inflation/deflation of the balloon lobes 14A/14B. A guide wire seal (not shown) is provided at the distal end of the elongate shaft 12 to provide a fluid seal about the guide wire 90. The infusion ports 15 are in fluid communication with the infusion lumen 13 which may be used for delivering infusion fluid independent of inflating/deflating the balloon lobes 14A/14B.

The manifold 16 may comprise a conventional "Y" adapter including a guide wire arm 24 and an inflation arm 26. The guide wire arm 24 and the inflation arm 26 may be in fluid communication with each other or fluidly independent, depending on the particular embodiment of the catheter 10 being implemented. A compression fitting (not shown) may be connected to the guide wire arm 24 to selectively provide a fluid tight seal about the guide wire 90, and to selectively lock the guide wire 90 relative to the catheter 10. The inflation arm 26 may be connected to a fluid source (not shown) such as a syringe or other inflation device to selectively inflate and deflate the balloon 14. The fluid source or inflation device may carry the inflation fluid and/or the infusion fluid.

A pressure relief valve 30, which is schematically illustrated in FIG. 1A, may be incorporated into the manifold 16 to prevent over pressurization of the balloon 14. The relief valve 30 is particularly beneficial for use in combination with the highly compliant balloon 14 which is adapted to be inflated to relatively low pressures. The relief valve 30 may be incorporated into the manifold 16 as shown, or any other part of the catheter 10 in fluid communication with the common lumen 18. For example, the relief valve 30 may be incorporated into the elongate shaft 12 adjacent the proximal end thereof.

The relief valve 30 includes a vent passage 32 which vents the inflation fluid therethrough at pressures above a predetermined threshold pressure. The predetermined threshold pressure may be selected to correspond to a pressure slightly below the rated burst pressure of the balloon 14, which may be approximately 1.5 ATM. Alternatively, the threshold pressure may be selected to correspond to a nominal inflated diameter of the balloon 14. For example, if the balloon 14 reaches a nominal diameter of 3.0 millimeters at 1.5 ATM, the pressure relief valve 30 may vent inflation fluid through the vent passage 32 at pressures above 1.5 ATM. As a further alternative, the threshold pressure may be selected to correspond to a maximum drug infusion rate. Those skilled in the art will recognize that the threshold pressure may be varied depending on the performance characteristics of the balloon 14 and the desired drug infusion rate.

Radiopaque marker bands 28 may be disposed on the elongate shaft 12 adjacent to the connection between the balloon 14 and the elongate shaft 12 to facilitate radiographic positioning of the balloon 14. The proximal marker band may be a split band of platinum or other radiopaque metal, and the distal marker band 28 may be a solid band of platinum or other radiopaque metal.

The construction of the elongate shaft 12 may be substantially similar to the catheter shaft constructions disclosed in U.S. patent application Ser. No. 09/311,446, filed May 14, 1999, entitled SINGLE LUMEN BALLOON-TIPPED MICRO CATHETER WITH REINFORCED SHAFT, the entire disclosure of which is hereby incorporated by reference.

For example, the elongate shaft 12 may include a proximal portion 36 and a distal portion 34. The proximal portion 36 may have an approximate length of 120 centimeters, an approximate inside diameter of 0.022 inches, and an approximate outside diameter of 0.037 inches. The distal portion 34 may have an approximate length of 30 centimeters, an approximate inside diameter of 0.018 inches, and an approximate outside diameter tapering from 0.037 inches to 0.030 inches. The distal seal 20 may have an inside diameter of approximately 0.010 inches to seal about the guide wire 90. Those skilled in the art will recognize that the length and diameter of the elongate shaft 12 may be adjusted depending on the particular portion of the patient's vascular system being navigated, and the particular guide wire 90 selected.

The proximal portion 36 of the elongate shaft 12 may comprise a single layer 38 of extruded polymer such as extruded polypropylene, which is commercially available under the trade name Profax 6743 from Himont. The single layer 38 of extruded polymer may be lap welded to the distal portion 34 of the elongate shaft 12. The distal portion 34 may include an extruded inner filler layer 40, a metallic braid layer 42 and an extruded outer filler layer 44. The inner filler layer 40, the outer filler layer 44 and the outer heat shrink layer 46 may extend to the distal end of the elongate shaft 12 adjacent the proximal end of the guide wire seal 20, while the braid layer 42 may terminate adjacent the proximal end of the balloon 14 for added flexibility. The proximal shaft portion 36 and the distal shaft portion 34 may be covered by an outer heat shrink layer 46 comprising an extruded polymer tube. The entire outer surface of the elongate shaft 12 may be covered with a hydrophilic polymer coating.

The inner filler layer 40 may comprise linear low density polyethelene commercially available from Dow, product number PE2517NT. The inner filler layer 40 extends from the proximal end of the distal shaft portion 34 and terminates adjacent the proximal end of the guide wire seal 20.

The metallic braid layer 42, which is disposed about the inner filler layer 40, may comprise an 8-strand braid of 0.003 inch by 0.0005 inch nickel titanium alloy ribbon. The braid layer 42 extends from the proximal end of the distal shaft portion 36 and terminates adjacent the proximal end of the balloon 14.

The outer filler layer 44 may comprise linear low density polyethelene commercially available from Dow, product number PE2517NT. The outer filler layer 44 is disposed about the metallic braid layer 42. The outer filler layer 44 extends from the proximal end of the distal shaft portion 34 and terminates adjacent proximal end of the guide wire seal 20.

The guide wire seal 20 may comprise a separate tip tube welded to the distal end of the elongate shaft 12, with the distal end of the balloon 14 extending partially over the distal tip. For example, the guide wire seal may comprise a separate tube of linear low density polyethylene welded to the distal end of the elongate shaft 12.

The outer heat shrink layer 46 may comprise an ethylene-vinyl acetate co-polymer commercially available from Dupont, product number ELVAX 460. The outer heat shrink layer 46 is heat shrunk over the single polymer layer 38 of the proximal shaft portion 36 and the outer filler layer 44 of the distal shaft portion 34. The outer heat shrink layer 46 extends from the proximal end of the elongate shaft 12 and terminates adjacent the proximal end of the guide wire seal 20.

In preparing the drug delivery balloon catheter 10 for use, the lumens 13/17/18/19 are flushed and the balloon 14 is partially inflated to remove air from the system using a flush syringe connected to the manifold 16. Once flushed, an inflation syringe or other inflation device is connected to the inflation arm 26 for subsequent inflation and deflation of the balloon 14 and/or drug infusion. The guide wire 90 is then advanced through the guide wire lumen 18/19 until the distal end of the guide wire 90 exists out the distal end of the shaft 12. The inflation syringe is then used to inflate the balloon 14 and inspect it for surface abnormalities and/or air bubbles. If air bubbles remain in the balloon 14, additional inflation fluid may be used to purge all air bubbles.

To position the drug delivery balloon catheter 10 in the patient's vascular system, an appropriate guiding catheter (not shown) may be placed in the vascular lumen using conventional techniques. The guide wire 90 and the drug delivery balloon catheter 10 are then inserted into the guide catheter until the distal tip of the catheter 10 reaches the distal end of the guide catheter. The balloon catheter 10 and guide wire 90 are alternatively advanced until the balloon 14 is positioned in the area of the vessel to be treated. The position of the balloon 14 relative to the desired treatment site in the patient's vascular system may be established using conventional radiographic techniques in combination with radiopaque markers 28.

With the balloon 14 placed in the center of the desired treatment site and the guide wire 90 advanced beyond the distal end of the shaft 12, the balloon 14 is then inflated using the inflation syringe by slowly infusing the desired volume of inflation fluid. In some embodiments, inflation fluid will immediately leak out of the infusion holes 15, and therefore it is desirable to quickly inflate the balloon 14 such that the balloon 14 engages the vascular wall or occlusive material without substantial loss of inflation fluid.

The inflation fluid may include saline, radiopaque contrast, and/or the desired drug or medication for treatment. Examples of suitable drugs used for dissolving ischemic clots include rTPA, reteplase, urikinase, etc. The radiopaque contrast contained in the inflation fluid allows visualization of the balloon 14 during inflation and provides visual feedback to the physician as to the effectiveness of infusion through the holes 15 and into the surrounding tissue at the treatment site. Examples of suitable drugs used for opening a vasospasm include papaverine. Those skilled in the art will recognize that virtually any desired drug may be utilized with the drug delivery balloon catheter 10 of the present invention.

If the drug delivery balloon catheter 10 illustrated in Figures 1A an 1B is used, the balloon lobe 14 and the infusion holes 15 are positioned to come into contact with the occlusive material or the location of the vasospasm. The balloon 14 is inflated to conform to the tissue at the treatment site. The inflation pressure may be increased intermittently to repeatedly angioplasty and infuse drug to the treatment site until the occlusive material is dissolved and/or the vasospasm is opened. The intermittent increase in inflation pressure results in pulsatile inflation of the balloon 14 and corresponding pulsatile infusion of the drug. In both the single lumen embodiment illustrated in FIGS. 2A and 2B and the multi-lumen embodiment illustrated in FIG. 2C, increasing the inflation pressure also increases the infusion pressure thereby increasing the flow of fluid through the infusion holes 15.

If the drug delivery balloon catheter 10 illustrated in FIGS. 3A an 3B is used, the tandem balloon lobes 14A/14B are positioned on either side of the occlusive material or the location of the vasospasm. The tandem balloons 14A/14B are inflated simultaneously by way of inflation ports 22. With this tandem arrangement, the infusion holes 15 are positioned adjacent the desired treatment site such that the balloon lobes 14A/14B trap the occlusive material/vasospasm therebetween thereby providing a highly concentrated pool of drug agent to treat the occlusive material/vasospasm. The infusion pressure may be increased intermittently to cause pulsatile jets of fluid to exit the infusion holes 15 to facilitate mechanical dissolution of occlusive material. If the single lumen embodiment illustrated in FIGS. 4A and 4B is used, increasing the inflation pressure also increases the infusion pressure thereby increasing the flow of fluid through the infusion holes. In the multi-lumen embodiment illustrated in FIG. 4C, the inflation pressure and the infusion pressure may be controlled independently.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular drug delivery balloon catheter, comprising:
   an elongate shaft having a proximal end and a distal end; and
   an inflatable balloon carried by the distal end of the shaft, the balloon comprising a compliant material such that the balloon elastically expands at an inflation pressure of less than 1.0 ATM, the balloon including a plurality of infusion holes.

2. An intravascular drug delivery balloon catheter as in claim 1, wherein the compliant material has a diametric compliance of 2.0 mm/ATM or more at inflation pressures less than 2.0 ATM.

3. An intravascular drug delivery balloon catheter as in claim 1, further comprising a relief valve in fluid communication with the balloon.

4. An intravascular drug delivery balloon catheter as in claim 3, wherein the relief valve vents at an inflation pressure of 1.5 ATM or more.

5. An intravascular drug delivery balloon catheter as in claim 1, wherein the infusion holes are open when the balloon is deflated and enlarge when the balloon is inflated.

6. An intravascular drug delivery balloon catheter as in claim 1, wherein the balloon defines two inflatable lobes.

7. An intravascular drug delivery balloon catheter as in claim 6, wherein the infusion holes are disposed between the lobes.

8. An intravascular drug delivery system, comprising:
   a balloon catheter comprising an elongate shaft having a proximal end, a distal end and an inflation lumen extending therethrough, an inflatable balloon connected to the distal end of the shaft, the balloon including a wall defining an interior in fluid communication with the inflation lumen, the balloon wall comprising a compliant material such that the balloon wall elastically expands at an inflation pressure of less than 1.0 ATM, the balloon wall including a plurality of infusion holes, the distal end of the shaft including a guidewire seal; and
   a guidewire disposed in the inflation lumen, the guidewire seal forming a fluid seal about the guidewire such that fluid passes from the inflation lumen, into the balloon, and through the infusion holes, and such that the guidewire is free to move relative to the guidewire seal.

9. An intravascular drug delivery system as in claim 8, wherein the compliant material has a diametric compliance of 2.0 mm/ATM or more at inflation pressures less than 2.0 ATM.

10. An intravascular drug delivery system as in claim 8, further comprising a relief valve in fluid communication with the balloon.

11. An intravascular drug delivery system as in claim 10, wherein the relief valve vents at an inflation pressure of 1.5 ATM or more.

12. An intravascular drug delivery system as in claim 8, wherein the infusion holes are open when the balloon is deflated and enlarge when the balloon is inflated.

13. An intravascular drug delivery system as in claim 8, wherein the balloon defines two inflatable lobes.

14. An intravascular drug delivery system as in claim 13, wherein the infusion holes are disposed between the lobes.

15. A method of delivering a drug intravascularly, the method comprising the steps of:

providing a drug delivery balloon catheter comprising an elongate shaft having a proximal end and a distal end, an inflatable balloon carried by the distal end of the shaft, the balloon comprising a compliant material such that the balloon elastically expands at an inflation pressure of less than 1.0 ATM, the balloon including a plurality of infusion holes which are open when the balloon is deflated and which enlarge when the balloon is inflated;

inserting the catheter into a patient's vasculature;

positioning the balloon adjacent a treatment site; and inflating the balloon such that the balloon elastically expands and the drug passes through the infusion holes.

16. A method of delivering a drug intravascularly as in claim 15, further comprising the step of increasing inflation pressure to increase infusion rate.

17. A method of delivering a drug intravascularly as in claim 16, wherein the step of increasing inflation pressure is pulsatile.

* * * * *

UNITED STATES PATENT AND TRADEMARK OFFICE
CERTIFICATE OF CORRECTION

PATENT NO.    : 6,623,452 B2
DATED         : September 23, 2003
INVENTOR(S)   : Thomas Yung-Hui Chien et al.

It is certified that error appears in the above-identified patent and that said Letters Patent is hereby corrected as shown below:

<u>Column 8,</u>
Please replace Claim 1 with the following:

1. An intravascular drug delivery balloon catheter, comprising:

an elongate shaft having a proximal end and a distal end, the elongate shaft including an inflatiuon lumen extending for at least a portion of its length; and an inflatable balloon carried by the distal end of the shaft, the balloon comprising a compliant material such that the balloon elastically expands at an inflation pressure of less than 1.0 ATM, the balloon including a plurality of infusion holes, the balloon being in fluid communication with the inflation lumen.

Signed and Sealed this

Twenty-seventh Day of April, 2004

JON W. DUDAS
*Acting Director of the United States Patent and Trademark Office*